United States Patent [19]

Thibault

[11] 4,345,935

[45] Aug. 24, 1982

[54] 2,4-IMIDAZOLIDINEDIONES, COMPOSITIONS AND HERBICIDAL METHOD

[75] Inventor: Thomas D. Thibault, Indianapolis, Ind.

[73] Assignee: Eli Lilly and Company, Indianapolis, Ind.

[21] Appl. No.: 308,621

[22] Filed: Oct. 5, 1981

[51] Int. Cl.$^3$ .................. A01N 43/50; C07D 233/96
[52] U.S. Cl. ............................................ 71/92; 71/76; 71/77; 424/273 R; 548/313
[58] Field of Search ............................ 548/313; 71/92

[56] References Cited

U.S. PATENT DOCUMENTS

| | | | |
|---|---|---|---|
| 3,216,816 | 9/1965 | Luckenbaugh | 71/2.5 |
| 3,822,282 | 7/1974 | Singer | 260/309.5 |
| 3,923,827 | 12/1975 | Dixon et al. | 260/309.6 |
| 3,925,553 | 12/1975 | Singer | 424/273 |
| 4,036,850 | 7/1977 | Enders | 260/309.5 |
| 4,248,620 | 2/1981 | Singer | 71/92 |

FOREIGN PATENT DOCUMENTS

| | | |
|---|---|---|
| 743708 | 12/1969 | Belgium . |
| 3619 | 8/1979 | European Pat. Off. . |
| 1039302 | 9/1958 | Fed. Rep. of Germany . |
| 2065977 | 8/1977 | Fed. Rep. of Germany . |
| 6902608 | 2/1968 | Netherlands . |
| 1247397 | 9/1971 | United Kingdom . |

OTHER PUBLICATIONS

Derwent Abstract No. 33439Y, Mar. 28, 1977.
Derwent Abstract No. 38201W, Jan. 27, 1973.

*Primary Examiner*—Robert W. Ramsuer
*Attorney, Agent, or Firm*—Charles W. Ashbrook; Arthur R. Whale

[57] ABSTRACT

5-(Dialkylamino)methylene-1,3-disubstituted-2,4-imidazolidinediones are useful herbicidal agents.

31 Claims, No Drawings

2,4-IMIDAZOLIDINEDIONES, COMPOSITIONS AND HERBICIDAL METHOD

BACKGROUND OF THE INVENTION

This invention concerns 2,4-imidazolidine-diones which have a (dialkylamino) methylene substituent at the 5-position of the imidazolidine ring. The compounds have good herbicidal activity.

Several 2,4-imidazolidinediones which display herbicidal activity are known. U.S. Pat. No. 4,036,850 discloses a group of 1-aryl-5-alkylidene-2,4-imidazolidinediones which are said to be active as herbicides, fungicides, bactericides, nematocides, as well as coccidiostatics. German Pat. No. 1,039,302 describes a group of herbicidal 2,4-imidazolidinediones which are unsubstituted at the 5-position. U.S. Pat. Nos. 3,822,282 and 3,925,553 describe a series of 2,4-imidazolidinediones which require a polyhaloethylimine or a polylhalovinylimine group at the imidazolidine 5-position. Such compounds are said to be valuable herbicidal and fungicidal agents. A group of 5-carbamoylimino-2,4-imidazolidinediones which are allegedly useful as herbicides is disclosed in British Pat. No. 1,247,397.

The compounds of the present invention differ from those of the art in that a (dialkylamino)methylene group is attached at the imidazolidine 5-position. An object of this invention is to provide novel compounds having useful herbicidal activity. Another object is to provide a herbicidal method employing the new compounds.

SUMMARY OF THE INVENTION

This invention provides a group of 2,4-imidazolidinediones which bear a (dialkylamino) methylene group at the 5-position of the imidazolidine ring system. The invention is more particularly directed to compounds defined by the formula:

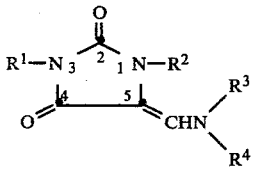

wherein:

$R^1$ and $R^2$ independently are lower alkyl, phenyl, or phenyl substituted with one or two groups selected from halo, lower alkyl, halo lower alkyl, lower alkoxy or nitro, and $R^3$ and $R^4$ independently are methyl or ethyl.

Preferred compounds according to this invention have the above formula wherein $R^1$ is phenyl or mono- or di-substituted phenyl, and $R^2$ is lower alkyl. Also preferred are compounds wherein $R^3$ and $R^4$ both are methyl.

A particularly preferred group of compounds are defined by the above formula wherein $R^1$ is phenyl, chlorophenyl, dichlorophenyl, methylphenyl, methoxyphenyl, nitrophenyl or trifluoromethylphenyl, $R^2$ is methyl, and $R^3$ and $R^4$ both are methyl.

Also provided by this invention are agricultural compositions comprising a 5-(dialkylamino)methylene-2,4-imidazolidinedione of the above formula together with a suitable carrier therefor.

A further embodiment of this invention is a method for controlling unwanted vegetative growth comprising applying to the locus where vegetative control is desired an effective amount of a compound defined by the above formula.

DETAILED DESCRIPTION OF THE INVENTION

As used herein, the term "lower alkyl" refers to groups such as methyl, ethyl, n-propyl, isopropyl, n-butyl, iso-butyl, tert-butyl, n-pentyl, and the like.

$R^1$ and $R^2$ in the above formula independently can be alkyl, phenyl or mono or disubstituted phenyl. Substituted phenyl groups include halo phenyl such as 2-chlorophenyl, 4-iodophenyl, 3-fluorophenyl, 2,3-dibromophenyl, 3-bromo-4-chlorophenyl, 2,4-difluorophenyl, and the like. Typical lower alkyl phenyl groups include 2-methylphenyl, 3-ethylphenyl, 4-isopropylphenyl, 3-tert-butylphenyl, 2-ethyl-3-methylphenyl, and related groups. Alkoxyphenyl groups include 2-methoxyphenyl, 3-ethoxyphenyl, 4-n-butoxyphenyl, 3-methoxy-4-n-butoxyphenyl, 2,4-dimethoxyphenyl, 2,6-dimethoxyphenyl, and 2-sec-butoxyphenyl. Typical halo lower alkyl phenyl groups include 2-trifluoromethylphenyl, 3-bromomethylphenyl, 4-trichloromethylphenyl, 2,6-di-trifluoromethylphenyl, and related groups. Nitrophenyl groups include 2-nitrophenyl, 3-nitrophenyl, 3,4-dinitrophenyl and the like. Other typical substituted phenyl groups include 2-chloro-4-methoxyphenyl, 3-ethoxy-4-nitrophenyl, 2-trifluoromethyl-4-tertbutylphenyl, 3-methyl-6-sec-butylphenyl and 3-n-propoxy-4-tert-butylphenyl.

The 5-(dialkylamino)methylene-2,4-imidazolidindiones provided by this invention can be prepared by reaction of a 5-unsubstituted 2,4-imidazolidindione with N,N-dimethyl (or diethyl) formamide dimethyl acetal. The 5-unsubstituted imidazolidinedione generally is derived by cyclization of a suitably substituted N-carbamoyl aminoacetic acid derivative, which in turn can be prepared by reaction of an isocyanate with an N-substituted amino-acetic acid derivative. The overall reaction is depicted by the following general scheme:

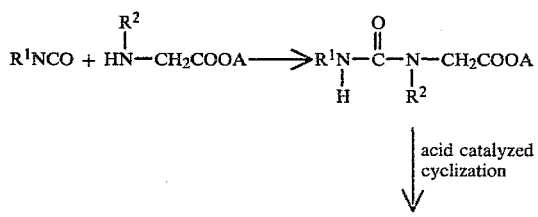

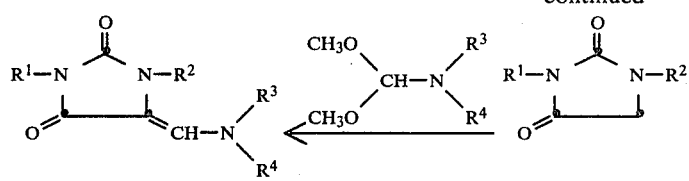

In the above scheme, $R^1$, $R^2$, $R^3$ and $R^4$ are as defined above, and A is hydrogen or lower alkyl such as methyl or ethyl.

The reaction of an isocyanate with an aminoacetic acid or ester to give the corresponding N-carbamoyl aminoacetic acid derivative, and the subsequent cyclization thereof to provide a 5-unsubstituted-2,4-imidazolidinedione can be carried out by the general procedure described in German Pat. No. 1,039,302. For example, an isocyanate such as phenylisocyanate is reacted with about an equimolar amount or slight excess of an N-alkylaminoacetic acid such as N-ethyl aminoacetic acid. The reaction generally is carried out in an aqueous media and in the presence of a base such as sodium hydroxide or the like. The reaction can also be conducted in an organic solvent such as toluene. The condensation is generally complete after about two hours to about five days when carried out at a temperature of about 10° to about 100° C. The product can be isolated by acidifying the reaction mixture, for example by the addition of a mineral acid, which normally causes precipitation of the product. Filtration affords the corresponding N-carbamoyl aminoacetic acid derivative. When an organic solvent is employed, it generally is simply removed by evaporation.

The N-carbamoyl aminoacetic acid derivative is readily cyclized to a 5-unsubstituted-2,4-imidazolidinedione by simply heating so as to eliminate water, or an alcohol in the base of an aminoacetic acid ester. The cyclization preferably is catalyzed by an aqueous mineral acid such as hydrochloric acid or the like. The cyclization is normally complete within about two to about four hours when carried out at about 50° to about 150° C. The 5-unsubstituted imidazolidinedione can be isolated by simply adding the reaction mixture to ice and subsequently collecting the precipitated product by filtration. Purification by recrystallization from common solvents can be carried out if desired.

The 5-(dialkylamino)methylene-2,4-imidazolidinediones provided by this invention are then prepared by reaction of the 5-unsubstituted-2,4-imidazolidinedione with an excess of an acetal of N,N-dimethyl or diethyl formamide, for instance the dimethyl acetal. The reaction generally is carried out by simply dissolving the 5-unsubstituted-2,4-imidazolidinedione in an excess of the dimethyl or diethyl formamide acetal and heating the reaction solvent to about 50° to about 100° C. for about eight to about forty-eight hours. The product of the reaction, a 5-(dialkylamino)methylene-2,4-imidazolidinedione of the invention, is readily isolated by cooling the reaction mixture to room temperature and then filtering the solid precipitate. Further purification normally is not required but can be accomplished if desired by conventional methods, including crystallization from common organic solvents such as ethyl acetate, diethyl ether, and the like.

Illustrative of the compounds embraced by this invention are the following:

5-(dimethylamino)methylene-1-ethyl-3-(3-bromophenyl)-2,4-imidazolidinedione;
5-(diethylamino)methylene-1-isopropyl-3-(4-difluoromethylphenyl)-2,4-imidazolidinedione;
5-(dimethylamino)methylene-1-n-butyl-3-(2,3-diethylphenyl)-2,4-imidazolidinedione;
5-(dimethylamino)methylene-1-methyl-3-(3-ethoxy-4-chlorophenyl)-2,4-imidazolidinedione;
5-(diethylamino)methylene-1-(4-ethoxyphenyl)3-ethyl-2,4-imidazolidinedione;
5-(dimethylamino)methylene-1,3-diethyl-2,4-imidazolidinedione;
5-(dimethylamino)methylene-1,3-diphenyl-2,4-imidazolidinedione;
5-(dimethylamino)methylene-1-sec-butyl-3-(2-fluoro-3-nitrophenyl)-2,4-imidazolidinedione;
5-(dimethylamino)methylene-1-n-propyl-3-(3,4-dinitrophenyl)-2,4-dimidazolidinedione;
5-(dimethylamino)methylene-1-ethyl-3-(3-trifluoromethylphenyl)-2,4-imidazolidinedione;
5-(dimethylamino)methylene-1-methyl-3-(2,6-dimethoxyphenyl)-2,4-imidazolidinedione;
5-(diethylamino)methylene-3-isopropyl-1-(4-ethoxyphenyl)-2,4-imidazolidinedione; and
5-(dimethylamino)methylene-1-methyl-3-(2,6-diethoxyphenyl)-2,4-imidazolidinedione.

The scope of novel 2,4-imidazolidinediones embraced by this invention will be further illustrated by the following detailed preparations and examples. The examples are not to be construed as limiting in any way.

EXAMPLE 1

5-(Dimethylamino)methylene-1-methyl-3-phenyl-2,4-imidazolidinedione

A. To a stirred solution of 70 g. of N-methylaminoacetic acid and 70 g. of sodium hydroxide in 500 ml. of water were added portion-wise over twenty minutes 100 g. of phenyl isocyanate. Following complete addition, the aqueous reaction mixture was stirred at 24° C. for two hours. The mixture was then filtered and the filtrate was acidified to pH 2 by the addition of conc. hydrochloric acid. The precipitate which formed was collected by filtration to provide N-methyl-N-carboxymethyl-N'-phenylurea.

B. The urea thus formed was dissolved in 250 ml. of fresh water containing 250 ml. of concentrated hydrochloric acid. The aqueous acidic reaction mixture was heated at reflux for three hours, and then poured onto 500 g. of ice. The precipitate which formed was collected by filtration and air dried to provide 35 g. of 1-methyl-3-phenyl-2,4-imidazolidinedione. M.P. 105°–106° C.

C. A solution of 35 g. of 1-methyl-3-phenyl-2,4-imidazolidinedione in 200 ml. of N,N-dimethylformamide dimethylacetal was heated at reflux for twelve hours. The reaction mixture was cooled to room temperature and concentrated, and the product then crystallized as a white solid. The solid was collected by filtration and dried to give 24 g. of 5-(dimethylamino)-methylene-1-methyl-3-phenyl-2,4-imidazolidinedione. M.P. 131°–133° C.

Analysis calc. for $C_{13}H_{15}N_3O_2$: Theory: C, 63.66; H, 6.16; N, 17.13; Found: C, 63.47; H, 5.89; N, 16.96.

EXAMPLE 2

5-(Dimethylamino)methylene-3-methyl-1-(3-trifluoromethylphenyl)-2,4-imidazolidinedione A. Ethyl N-(3-trifluoromethylphenyl)aminoacetate was prepared by reacting 3-trifluoromethylaniline with ethyl bromoacetate. To a solution of 66 g. of ethyl N-(3-trifluoromethylphenyl)aminoacetate in 700 ml of toluene were added in one portion 30 g. of methyl isocyanate. The reaction mixture was heated at reflux for twenty hours, and then cooled and an additional 20 g. of methyl isocyanate were added. Again the reaction mixture was heated at reflux for twenty hours, after which time it was cooled, and an additional 20 g. of methyl isocyanate were added. The mixture was heated at reflux for four days, and then cooled and the solvent was removed by evaporation under reduced pressure to give an oil.

B. The oil thus formed was dissolved in 500 ml. of 6 N hydrochloric acid and the reaction mixture was heated at reflux for three hours. The mixture was next added to 500 g. of ice, and the precipitate which formed was collected by filtration. The precipitate was crystallized from ethyl acetate to afford 36.5 g. of 3-methyl-1-(3-trifluoromethylphenyl)-2,4-imidazolidinedione. M.P. 87°–88° C.

Analysis calc. for $C_{11}H_9F_3N_2O_2$: Theory: C, 51.17; H, 3.51; N, 10.85; F, 22.07; Found: C, 51.27; H, 3.48; N, 11.06; F, 22.31.

C. A solution of 25 g. of 3-methyl-1-(3-trifluoromethylphenyl)-2,4-imidazolidinedione in 125 ml. of N,N-dimethylformamide dimethylacetal was heated at reflux for forty-eight hours. The reaction mixture was cooled and the volume was reduced by concentration under reduced pressure. The white crystalline product which formed was collected by filtration and recrystallized from ethyl acetate to afford 17 g. of 5-(dimethylamino)-methylene-3-methyl-1-(3-trifluoromethylphenyl)2,4-imidazolidinedione. M.P. 103°–104° C.

Analysis calc. for $C_{14}H_{14}F_3N_3O_2$: Theory: C, 53.68; H, 4.50; N, 13.41; F, 18.19; Found: C, 53.89; H, 4.52; N, 13.63; F, 18.11.

By following the general procedures set forth above in Examples 1 and 2, the following 5-(dimethylamino)-methylene-2,4-imidazolidinediones were prepared by reaction of the corresponding 5-unsubstituted-2,4-imidazolidinedione with N,N-dimethylformamide dimethylacetal.

EXAMPLE 3

5-(Dimethylamino)methylene-1-methyl-3-(3-methylphenyl)-2,4-imidazolidinedione

M.P. 120°–121° C.

Analysis calc. for $C_{14}H_{17}N_3O_2$; Theory: C, 64.85; H, 6.61; N, 16.20; Found: C, 64.72; H, 6.47; N, 15.99.

EXAMPLE 4

5-(Dimethylamino)methylene-1-methyl-3-(4-methylphenyl)-2,4-imidazolidinedione

M.P. 162°–164° C.

Analysis calc. for $C_{14}H_{17}N_3O_2$: Theory: C, 64.85; H, 6.61; N, 16.20; Found: C, 64.65; H, 6.36; N, 16.13.

EXAMPLE 5

5-(Dimethylamino)methylene-1-methyl-3-(2-chlorophenyl)-2,4-imidazolidinedione

M.P. 149°–150° C.

Analysis calc. for $C_{13}H_{14}ClN_3O_2$: Theory: C, 55.82; H, 5.04; N, 15.02; Found: C, 55.53; H, 5.09; N, 14.80.

EXAMPLE 6

5-(Dimethylamino)methylene-1-methyl-3-(3-chlorophenyl)-2,4-imidazolidinedione

M.P. 110°–112° C.

Analysis calc. for $C_{13}H_{14}ClN_3O_2$: Theory: C, 55.82; H, 5.04; N, 15.02; Cl, 12.67; Found: C, 55.89; H, 4.96; N, 15.05; Cl, 12.80.

EXAMPLE 7

5-(Dimethylamino)methylene-1-methyl-3-(4-chlorophenyl)-2,4-imidazolidinedione

M.P. 171°–173° C.

Analysis calc. for $C_{13}H_{14}ClN_3O_2$: Theory: C, 55.82; H, 5.04; N, 15.02; Cl, 12.67; Found: C, 55.53; H, 4.80; N, 15.23; Cl, 12.89.

EXAMPLE 8

5-(Dimethylamino)methylene-1-methyl-3-(3,4-dichlorophenyl)-2,4-imidazolidinedione

M.P. 132°–134° C.

Analysis calc. for $C_{13}H_{13}Cl_2N_3O_2$: Theory: C, 49.70; H, 4.17; N, 13.38; Found: C, 49.47; H, 4.08; N, 13.25.

EXAMPLE 9

5-(Dimethylamino)methylene-1-methyl-3-(3-trifluoromethylphenyl)-2,4-imidazolidinedione

M.P. 132°–134° C.

Analysis calc. for $C_{14}H_{14}F_3N_3O_2$: Theory: C, 53.68; H, 4.50; N, 13.41; F, 18.19; Found: C, 53.65; H, 4.43; N, 13.44; F, 18.42.

EXAMPLE 10

5-(Dimethylamino)methylene-1-methyl-3-(4-methoxyphenyl)-2,4-imidazolidinedione

M.P. 182°–184° C.

Analysis calc. for $C_{14}H_{17}N_3O_3$: Theory: C, 61.08; H, 6.22; N, 15.26; Found: C, 61.26; H, 6.09; N, 15.42.

EXAMPLE 11

5-(Dimethylamino)methylene-1-methyl-3-(3-nitrophenyl)-2,4-imidazolidinedione

M.P. 179°–180° C.

Analysis calc. for $C_{13}H_{14}N_4O_4$: Theory: C, 53.79; H, 4.86; N, 19.30; Found: C, 53.52; N, 4.68; N, 19.02.

The 5-(dimethylamino)methylene-2,4-imidazolidinediones provided by this invention have been found to display useful pre- and post-emergence herbicidal activity against a variety of weed species commonly occurring in areas utilized for growing desired crops such as the cereal grains, corn, soybeans and the like. The selective herbicidal activity of the compounds has been analyzed in a number of standard greenhouse tests. One such test was a broad spectrum greenhouse test carried out by filling square plastic pots with a sterilized sandy loam soil and planting seeds of tomato, large crabgrass and pigweed. Each pot was fertilized with 158 mg. of a 23-21-17 fertilizer four days before treatment with test compound.

The test compounds were formulated for application by dissolving each compound in a solution comprising 100 ml. of acetone and 100 ml. of ethanol plus 1.174 g. of Tomixul R and 0.783 g. of Toximul S. (Toximul R and Toximul S are proprietary blends of anionic and nonionic surfactants manufactured by Stepan Chemical Company, Northfield, Ill.). Each test compound was dissolved in the diluent at the rate of 20 mg. per 2 ml. of solvent, and then the solution was diluted to 8 ml. with deionized water. The formulated compounds were applied to the planted pots at an effective rate of 15 pounds per acre (16.8 kg/ha).

Test compounds were applied postemergence to some planted pots and preemergence to others. The postemergence applications were made by spraying the solution containing the test compound over the emerged plants about twelve days after the seeds were planted. Preemergence applications were sprayed on the soil one day after the seeds were planted.

Following application of the test compounds, the pots were placed in a greenhouse and watered as necessary. Observations were conducted about 10–13 days following application of the test compounds, and untreated control plants were used as standards in each observation. The degree of herbicidal activity of the test compounds was determined by rating the treated plants on a scale of 1–5. On this scale, "1" indicates no plant injury; "2" is slight injury; "3" is moderate plant injury; "4" is severe injury and "5" is death of the plant or no seedling emergence. The type of plant injury sustained by the plants was tabulated using the following code letters:

A = abscission of leaves
B = burned
C = chlorsis
D = death
E = epinasty
S = stunting

TABLE I

| Compound of Example No. | Preemergence | | | Postemergence | | |
| --- | --- | --- | --- | --- | --- | --- |
| | Tomato | Large Crab-grass | Pig-weed | Tomato | Large Crab-grass | Pig-weed |
| 1 | 2BS | 3BS | 3BS | 5D | 2BS | 5D |
| 2 | 3BS | 3BS | 3S | 4BS | 3BS | 3BS |
| 3 | 3BS | 4BS | 4BS | 5D | 5D | 5D |
| 4 | 3BS | 3BS | 3S | 5D | 1 | 3BS |
| 5 | 2BS | 3BS | 2BS | 2B | 2B | 2B |
| 6 | 3BS | 3BS | 3BS | 5D | 5D | 3BS |
| 7 | 3S | 3BS | 3BS | 5D | 5D | 5D |
| 9 | 4BS | 4BS | 4BS | 5D | 2B | 2B |
| 10 | 2SC | 3S | 4BS | 4BS | 1 | 2BS |
| 11 | 1 | 1 | 1 | 1 | 1 | 1 |

A similar greenhouse study utilizing seven seed species was carried out to further evaluate preemergence and postemergence herbicidal activity of the 5-(dimethylamino)methylene-2,4-imidazolidinediones of this invention. The compounds to be evaluated were formulated according to the procedure outlined above, except that about 4 g/100 ml of the compound were dissolved in the surfactant-containing solvent, and about 1 part of the organic solution was diluted with 12 parts of water before application to seeded containers. The compounds were applied at the effective rate of 8 lbs/acre (8.97 kg/ha). Typical results of such evaluation are presented in Table II below.

TABLE II

| Compound of Example Number | Preemergence | | | | | | | Postemergence | | | | | | |
| --- | --- | --- | --- | --- | --- | --- | --- | --- | --- | --- | --- | --- | --- | --- |
| | Corn | Large Crab-grass | Pig-weed | Foxtail | Velvet Leaf | Morning-glory | Zinnia | Corn | Large Crab-grass | Pig-weed | Foxtail | Velvet Leaf | Morning-glory | Zinnia |
| 1 | 3 | 5 | 5 | 4 | 5 | 4 | 3 | 1 | 1 | 2 | 1 | 2 | 1 | 2 |
| 2 | 1 | 4 | 4 | 3 | 2 | 1 | 3 | 1 | 1 | 1 | 1 | 2 | 2 | 3 |
| 3 | 1 | 5 | 5 | 3 | 5 | 2 | 3 | 1 | 1 | 4 | 1 | 3 | 2 | 3 |
| 4 | 1 | 4 | 4 | 3 | 4 | 3 | 4 | 1 | 1 | 1 | 1 | 2 | 1 | 1 |
| 5 | 1 | 3 | 3 | 3 | 3 | 1 | 3 | 1 | 1 | 2 | 1 | 2 | 2 | 2 |
| 6 | 3 | 5 | 5 | 5 | 5 | 3 | 5 | 1 | 1 | 4 | 1 | 3 | 2 | 3 |
| 7 | 2 | 5 | 5 | 5 | 5 | 3 | 3 | 1 | 1 | 3 | 1 | 1 | 1 | 1 |
| 8 | 2 | 5 | 5 | 4 | 5 | 5 | 5 | 1 | 2 | 5 | 1 | 3 | 4 | 4 |
| 9 | 3 | 5 | 4 | 5 | 4 | 3 | 3 | 1 | 1 | 2 | 1 | 2 | 2 | 2 |
| 10 | 1 | 3 | 3 | 2 | 3 | 1 | 2 | 1 | 1 | 1 | 1 | 1 | 1 | 1 |
| 11 | 2 | 3 | 2 | 3 | 1 | 1 | 3 | 1 | 1 | 1 | 1 | 1 | 2 | 2 |

The herbicidal activity of a number of the compounds of the invention was evaluated at various application rates in a multiple-species greenhouse test. Several additional weed and crop species were utilized to determine the herbicidal selectivity of the compounds. The compounds were formulated as described above, and applied preemergence to seeded flats. The results for several compounds of the invention are presented below in Table III.

TABLE III

Preemergence

| Compound of Example No. | Rate of Application Lbs/Acre | (kg/ha) | Corn | Cotton | Soybean | Wheat | Alfalfa | Sugar Beet | Rice | Cucumber | Tomato | Barnyard Grass | Lambsquarter | Large Crabgrass | Mustard | Pigweed | Foxtail | Wildoat | Velvetleaf | Jimson Weed | Morningglory | Zinnia |
|---|---|---|---|---|---|---|---|---|---|---|---|---|---|---|---|---|---|---|---|---|---|---|
| 1 | 4 | (4.5) | 1 | 1 | 2 | 3 | 2 | 4 | 3 | 3 | 2 | 3 | 5 | 5 | 4 | 5 | 4 | 3 | 4 | 3 | 2 | 3 |
|  | 2 | (2.24) | 1 | 2 | 2 | 2 | 1 | 3 | 3 | 3 | 1 | 1 | 5 | 4 | 3 | 4 | 3 | 1 | 4 | 3 | 2 | 2 |
|  | 1 | (1.12) | 1 | 3 | 1 | 3 | 1 | 2 | 1 | 3 | 4 | 3 | 5 | 4 | 3 | 5 | 3 | 1 | 3 | 1 | 1 | 3 |
|  | 0.5 | (0.56) | 2 | 1 | 1 | 1 | 1 | 2 | 2 | 2 | 2 | 1 | — | 1 | 1 | 2 | 3 | 1 | 2 | 1 | 1 | 2 |
| 2 | 4 | (4.5) | 1 | 1 | 1 | 1 | 1 | 1 | 1 | 1 | 1 | 1 | — | 4 | 1 | 2 | 2 | 1 | 4 | 2 | 1 | 1 |
|  | 2 | (2.24) | 1 | 1 | 1 | 1 | 2 | 1 | 1 | 1 | 1 | 1 | — | 2 | 1 | 1 | 1 | 1 | 2 | 1 | 1 | 2 |
|  | 1 | (1.12) | 1 | 1 | 1 | 1 | 1 | 1 | 1 | 1 | 1 | 1 | — | 1 | 1 | 1 | 1 | 1 | 1 | 1 | 1 | 1 |
| 3 | 4 | (4.5) | 1 | 1 | 1 | 1 | 1 | 4 | 1 | 2 | 1 | 1 | 5 | 5 | 4 | 3 | 3 | 2 | 5 | 4 | 3 | 3 |
|  | 2 | (2.24) | 1 | 1 | 1 | 1 | 1 | 1 | 1 | 2 | 1 | 1 | 3 | 4 | 1 | 3 | 2 | 1 | 4 | 1 | 1 | 2 |
|  | 1 | (1.12) | 1 | 1 | 1 | 1 | 1 | 1 | 1 | 2 | 1 | 1 | 2 | 3 | 1 | 1 | 1 | 1 | 2 | 1 | 1 | 2 |
| 4 | 4 | (4.5) | 2 | 1 | 1 | 1 | 2 | 1 | 2 | 1 | 1 | 1 | — | 4 | 2 | 2 | 2 | 2 | 4 | 3 | 2 | 3 |
|  | 2 | (2.24) | 2 | 1 | 1 | 1 | 3 | 3 | 1 | 2 | 1 | 1 | — | 4 | 3 | 5 | 2 | 1 | 3 | 2 | 2 | 3 |
|  | 1 | (1.12) | 2 | 1 | 1 | 1 | 2 | 2 | 2 | 2 | 1 | 1 | — | 3 | 2 | 2 | 2 | 3 | 2 | 1 | 1 | 3 |
| 6 | 4 | (4.5) | 1 | 1 | 1 | 1 | 1 | 3 | 1 | 3 | 3 | 3 | 4 | 4 | 5 | 4 | 5 | 4 | 1 | 3 | 2 | 3 |
|  | 2 | (2.24) | 1 | 1 | 1 | 1 | 1 | 3 | 2 | 2 | 3 | 3 | 4 | 4 | 2 | 5 | 2 | 1 | 3 | 2 | 2 | 2 |
|  | 1 | (1.12) | 1 | 1 | 1 | 1 | 1 | 3 | 1 | 2 | 2 | 3 | 3 | 3 | 2 | 2 | 2 | 1 | 2 | 1 | 1 | 1 |
| 7 | 4 | (4.5) | 1 | 1 | 1 | 1 | 1 | 5 | 5 | 2 | 3 | 3 | 4 | 4 | 4 | 4 | 4 | 3 | 2 | 4 | 5 | 3 |
|  | 2 | (2.24) | 1 | 1 | 2 | 3 | 1 | 5 | 3 | 2 | 2 | 3 | 4 | 4 | 2 | 4 | 3 | 2 | 4 | 2 | 3 | 3 |
|  | 1 | (1.12) | 1 | 1 | 1 | 1 | 1 | 4 | 1 | 2 | 4 | 2 | 4 | 4 | 4 | 4 | 4 | 1 | 4 | 1 | 1 | 5 |
| 8 | 4 | (4.5) | 1 | 1 | 2 | 1 | 1 | 3 | 1 | 2 | 2 | 4 | 4 | 4 | 4 | 2 | 2 | 2 | 4 | 5 | 5 | 3 |
|  | 2 | (2.24) | 2 | 1 | 1 | 1 | 1 | 2 | 2 | 2 | 1 | 3 | 3 | 3 | 2 | 2 | 3 | 1 | 2 | 2 | 2 | 2 |
|  | 1 | (1.12) | 1 | 1 | 1 | 1 | 1 | 1 | 1 | 1 | 1 | 2 | 3 | 3 | 3 | 4 | 1 | 1 | 1 | 1 | 1 | 1 |
| 9 | 4 | (4.5) | 2 | 2 | 1 | 1 | 1 | 4 | 2 | 3 | 2 | 3 | 3 | 3 | 4 | 2 | 4 | 4 | 1 | 4 | 2 | 2 |
|  | 2 | (2.24) | 1 | 1 | 1 | 1 | 1 | 3 | 1 | 1 | 1 | 3 | 3 | 3 | 3 | 2 | 3 | 1 | 1 | 2 | 1 | 2 |
|  | 1 | (1.12) | 1 | 1 | 1 | 1 | 1 | 3 | 1 | 1 | 1 | 2 | 1 | 1 | 1 | 3 | 1 | 1 | 1 | 2 | 1 | 1 |

The compound of Example 8, 5-(dimethylamino)-methylene-1-methyl-3-(3,4-dichlorophenyl)-2,4-imidazolidinedione, was further evaluated as a herbicide in open field studies. The compound was applied to individual test plots seeded to wheat, barley, cotton, cucumber and soybeans. The herbicidal activity of the compound was compared to that of linuron, a widely used commercial herbicide. At rates of 1.0, 2.0, 3.0 and 4.0 pounds per acre, both the test compound and the reference herbicide failed to provide the desired degree of weed control. Lack of significant rainfall during the test period is believed to have caused the poor results. In a subsequent field evaluation on plots seeded to corn and grain sorghum, the test compound demonstrated good control of foxtail millet and pigweed at rates of 3.0 and 4.0 pounds per acre. Adequate control of jimsonweed was observed at 4.0 pounds per acre. Rain fell the day following application of the herbicide, thereby suggesting that rainfall contributes to the activation of the compounds of this invention. This is true with numerous other herbicides, including linuron.

As the data presented hereinabove indicate the 5-(dialkylamino)methylene-2,4-imidazolidinediones provided by this invention possess useful selective herbicidal activity and therefore are of particular value in the control and elimination of undesired vegetative growth. One embodiment of this invention is a method for controlling undesired plant growth which comprises applying to plants whose growth is to be controlled or to the soil where such undesired plants are growing a herbicidally effective amount of a compound defined herein by the above general formula. A "herbicidally effective amount" as used herein will generally be an amount from about 0.1 to about 15.0 pounds of imidazolidinedione per acre of soil (ie. about 0.112 to about 16.8 kg/ha). The compounds are more preferably applied at rates of about 0.5 to about 10.0 pounds per acre (about 0.56 to about 11.2 kg/ha). The compounds are effective in controlling undesired vegetative growth when applied directly to the plant, for instance to the foliage when the plants are young, but are preferably employed by application to the soil prior to plant emergence. If desired, the compounds can be incorporated into the soil, for instance by use of a conventional double disc or harrow prior to seeding to desired plants such as corn, soybeans, wheat and the like. It is preferred, however, that the compound simply be applied without incorporation to the soil before plant emergence, and that the compounds be permitted to leach into the soil with the assistance of natural rainfall. While the compounds are thus effective in the control of a wide variety of broadleaf and grassy weeds, a preferred practice of the invention is in the control of weeds such as pigweed, foxtail, velvet leaf, and morningglory.

In still another embodiment of the invention there is provided a herbicidal composition comprising a 5-(dialkylamino)methylene-2,4-imidazolidinedione of the above formula together with a suitable agricultural excipient, carrier or diluent. Such compositions generally will contain from about 0.1 to about 95.0 percent by weight of active ingredient. The particular amount of imidazolidinedione will of course be determined by the specific type of composition desired. Sprayable formulations are preferred, because of the rapidity and economy of application, and because sprayed applications do not drift to untreated areas as much as dusts do. Granular formulations may be used when the compounds are to be applied to the soil.

The inert portions of agricultural chemical formulations and the methods of manufacture of them are well known and conventional in the agricultural chemicals art. Only a brief explanation of such formulations containing the compounds of this invention will therefore be given.

Dusts containing the compounds usually contain from about 0.1 to about 5 percent of the compound. Dusts are prepared by intimately mixing and finely grinding the compound with an inert solid such as ground montmorillonite clay, attapulgus clay, talc, ground volcanic rock, kaolin clay, or other inert, relatively dense, inexpensive substance.

The most convenient formulations are in the form of concentrated compositions to be applied by spraying as water dispersions or emulsions containing in the range from about 0.01 percent to about 5 percent of the compounds. Water-dispersible or emulsifiable compositions may be either solids usually known as wettable powders, or liquids usually known as emulsifiable concentrates.

A typical wettable powder comprises an intimate mixture of a compound of the invention, an inert carrier, and surfactants. The concentration of the active compound is usually from about 5 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent of the wettable powder, are chosen from among the sulfonated lignins, the condensed napthalenesulfonates, the napthalenesulfonates, the alkylbenzenesulfonates, the alkyl sulfates and nonionic surfactants such as ethylene oxide adducts of phenol.

A typical emulsifiable concentrate comprises from about 0.1 to about 4 lbs. of a compound of the invention per gallon of liquid, dissolved in a mixture of organic solvents and emulsifiers. The organic solvent is chosen with regard to its solvency and its cost. Useful solvents include the aromatics, especially the xylenes, and the hydrophilic solvents such as the higher alcohols, glycols such as ethylene glycol, and the hydroxy ethers such as 2-ethoxyethanol. Other organic solvents may also be used, including the terpenic solvents such as rosin and turpentine derivatives. Suitable emulsifiers for emulsifiable concentrates are chosen from the same types used for wettable powders, and are used at similar percentages.

Solid, granular compositions are convenient for the application of compounds of this invention to the soil. Granules comprise a compound of the invention dispersed on a granular inert carrier such as coarsely ground clay of from about 0.1 to about 3 mm. particle size. The compound is most conveniently applied to the clay by dissolving it in an inexpensive solvent and applying the solution to the sized clay in an appropriate solids mixer.

The formulated compounds are applied to plants in the manners conventional in agricultural chemistry. Sprayable compositions are easily applied by any of many types of sprayers available to the art. Self-propelled, tractor-mounted, and towed spray devices which apply the water-dispersed formulations through calibrated atomizing nozzles are available and effective. Metering applicators are also available which can apply accurately measured quantities of granular compositions to the soil. The operator of the application equipment need only take care to adjust the equipment to apply an amount of the water-dispersed or granular formulation per acre which supplies the desired application rate of the compound, and to apply the amount uniformly to the plants to be treated.

The compositions provided herein can additionally contain other herbicides, for instance a urea such as linuron, a dinitroaniline such as trifluralin, a triazine such as metribuzin, an aniline such metalachlor or alachlor, and similar well known herbicides. Such compositions will generally take the form of a tank mix or the like.

The following examples provide an illustration of typical herbicidal compositions comprehended by this invention.

EXAMPLE 12

| Wettable Powder | |
|---|---|
| Ingredient | Concentration Weight (%) |
| 5-(dimethylamino)methylene-1-methyl-3-(3,4-dichlorophenyl)-2,4-imidazolidinedione | 50 |
| Igepal CA=6.30, a polyoxyethylene octyl phenol nonionic wetting agent-GAF Corp. | 20 |
| Bardens Clay | 30 |

The imidazolidinedione herbicide is finely divided into a powder and blended to uniformity with the adjuvants to form a free flowing powder that will be wetted and suspendable in water at or near the site of application to form a sprayable mixture. The composition is then sprayed on the locus where vegetative control is desired. The application is done at a volume rate so that the active ingredient is present at about 1 to about 4 pounds per acre.

EXAMPLE 13

| Dust | |
|---|---|
| Ingredient | Weight % |
| 5-(dimethylamino)methylene-1-ethyl-3-(4-methoxyphenyl)2,4-imidazolidinedione | 5 |
| Diatomite, a diatomaceous earth, Witco Chemical Corp., Inorganic Specialities Division | 95 |

The imidazolidinedione is suspended in acetone and sprayed onto the diatomaceous earth diluent. The solvent is then removed by evaporation and the dry mixture is ground to a fine powder of uniform particle size of about 10 to about 40 microns. The dust formulation can be diluted at the site of application if desired by the addition of additional excipient such as silica or clay. The dust is surface applied to the soil or plants where vegetative control is desired, either by conventional ground equipment or aerially.

EXAMPLE 14

| Tank Mix | |
|---|---|
| Ingredient | Weight % |
| 5-(dimethylamino)methylene-1-phenyl-3-ethyl-2,4-imidazolidinedione | 60 |
| N,N-di-n-propyl-2,6-dinitro-3-amino-4-trifluoromethylaniline (prodiamine) | 40 |

A wettable powder formulation containing 50% by weight of the imidazolidinedione is added to an agitated aqueous suspension of an emulsifiable concentrate formulation containing 25% by weight of the dinitroaniline herbicide. The mixture is agitated and sprayed onto the soil surface at the rate of about 3 pounds per acre of imidazolidinedione and about 2 pounds per acre of the dinitroaniline. The soil can then be seeded to soybeans or the like, and the crop is grown substantially free of unwanted vegetation such as crabgrass, foxtail, fall panicum, purslane and the like.

While the novel compounds of this invention are especially useful as herbicides, they are valuable in the treatment and control of several other plant and animal diseases. For example, the compounds have demonstrated activity against certain viruses such as rhinovirus, Ann Arbor and herpes virus, and they have demonstrated good plant growth regulator activity, for instance in altering root growth and shoot growth. Certain of the compounds have also demonstrated useful central nervous system activity in standard mice studies. Additionally, some of the compounds have demonstrated useful activity against various plant diseases. The compound of Example 10, for instance, showed good control of bacterial blight when applied to soil at 11 pounds per acre, and also demonstrated antifungal activity against anthracnose at a foliar concentration of 400 ppm. The compound of Example 5 completely controlled root knot nematode when applied to soil at 11 pounds per acre.

The compounds provided by this invention are additionally useful as intermediates in the synthesis of other valuable herbicidal agents. For example, reaction of a 5-(dialkylamino)methylene-2,4-imidazolidinedione defined herein with phosphorus oxychloride and dimethylformamide provides a 4-chloro-2-imidazolidinone-5-carboxaldehyde. Further reaction of the latter compound with an amine affords a 5-amino-imidazole-4-carboxaldehyde herbicide. The use of compounds of this invention as intermediates is more fully discussed in copending application Ser. No. 308,728 filed Oct. 5, 1981.

I claim:

1. A compound of the formula:

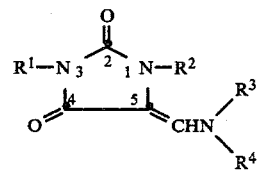

wherein: $R^1$ and $R^2$ independently are lower alkyl, phenyl, or phenyl substituted with one or two groups selected from halo, lower alkyl, halo lower alkyl, lower alkoxy or nitro, and $R^3$ and $R^4$ independently are methyl or ethyl.

2. The compound of claim 1 wherein $R^1$ is lower alkyl and $R^3$ and $R^4$ both are methyl.

3. The compound of claim 2 wherein $R^2$ is phenyl or mono- or di-substituted phenyl.

4. The compound of claim 3, said compound being 5-(dimethylamino)methylene-3-methyl-1-(3-trifluoromethylphenyl)-2,4-imidazolidinedione.

5. The compound of claim 1 wherein $R^2$ is lower alkyl and $R^3$ and $R^4$ both are methyl.

6. The compound of claim 5 wherein $R^1$ is phenyl or mono- or disubstituted phenyl.

7. The compound of claim 6 wherein $R^2$ is methyl.

8. The compound of claim 7 wherein $R^1$ is phenyl.

9. The compound of claim 7 wherein $R^1$ is chlorophenyl, dichlorophenyl, methylphenyl, methoxyphenyl, nitrophenyl or trifluoromethylphenyl.

10. The compound of claim 9 wherein $R^1$ is 2-chlorophenyl.

11. The compound of claim 9 wherein $R^1$ is 3-chlorophenyl.

12. The compound of claim 9 wherein $R^1$ is 4-chlorophenyl.

13. The compound of claim 9 wherein $R^1$ is 3-methylphenyl.

14. The compound of claim 9 wherein $R^1$ is 4-methylphenyl.

15. The compound of claim 9 wherein $R^1$ is 3-nitrophenyl.

16. The compound of claim 9 wherein $R^1$ is 4-methoxyphenyl.

17. The compound of claim 9 wherein $R^1$ is 3-trifluoromethylphenyl.

18. The compound of claim 9 wherein $R^1$ is 3,4-dichlorophenyl.

19. A herbicidal method for controlling undesired plant growth comprising applying to said undesired plants or the the soil where vegetative control is desired a herbicidally effective amount of a compound of claim 1.

20. The method of claim 19 employing a compound wherein $R^1$ is lower alkyl, $R^2$ is phenyl, mono- or disubstituted phenyl and $R^3$ and $R^4$ both are methyl.

21. The method of claim 19 employing a compound wherein $R^1$ is phenyl, mono- or disubstituted phenyl $R^2$ is lower alkyl and $R^3$ and $R^4$ both are methyl.

22. The method of claim 21 employing a compound wherein $R^2$ is methyl.

23. The method of claim 22 employing a compound wherein $R^1$ is phenyl, chlorophenyl, dichlorophenyl, methylphenyl, methoxyphenyl, nitrophenyl, or trifluoromethylphenyl.

24. The method of claim 23 employing a compound wherein $R^1$ is phenyl, 2-chlorophenyl, 3-chlorophenyl, 4-chlorophenyl, 3,4-dichlorophenyl, 3-methylphenyl, 4-methylphenyl, 3-nitrophenyl, 4-methoxyphenyl or 3-trifluoromethylphenyl.

25. A herbicidal composition comprising from about 0.1 to about 95.0 percent by weight of a compound of claim 1 admixed with a suitable agricultural carrier.

26. The composition of claim 25 employing a compound wherein $R^1$ is lower alkyl, $R^2$ is phenyl, mono- or disubstituted phenyl, and $R^3$ and $R^4$ both are methyl.

27. The composition of claim 26 employing a compound wherein $R^1$ is methyl and $R^2$ is 3-trifluoromethylphenyl.

28. The composition of claim 25 employing a compound wherein $R^1$ is phenyl, or mono- or disubstituted phenyl, $R^2$ is lower alkyl, and $R^3$ and $R^4$ both are methyl.

29. The composition of claim 28 employing a compound wherein $R^2$ is methyl.

30. The composition of claim 30 employing a compound wherein $R^1$ is phenyl, chlorophenyl, dichlorophenyl, methylphenyl, methoxyphenyl, nitrophenyl, or trifluoromethylphenyl.

31. The composition of claim 30 employing a compound wherein $R^1$ is 2-chlorophenyl, 3-chlorophenyl, 4-chlorophenyl, 3,4-dichlorophenyl, 3-methylphenyl, 4-methylphenyl, 3-nitrophenyl, 4-methoxyphenyl or 3-trifluoromethylphenyl.

* * * * *